(12) United States Patent
Dunfee et al.

(10) Patent No.: US 7,258,480 B2
(45) Date of Patent: Aug. 21, 2007

(54) APPARATUS FOR MIXING LIQUID SAMPLES USING A TWO DIMENSIONAL STIRRING PATTERN

(75) Inventors: William David Dunfee, Newark, DE (US); Robert Franklin Hazlewood, Jr., Newark, DE (US)

(73) Assignee: Dade Behring Inc., Deerfield, IL (US)

( * ) Notice: Subject to any disclaimer, the term of this patent is extended or adjusted under 35 U.S.C. 154(b) by 307 days.

(21) Appl. No.: 11/032,356

(22) Filed: Jan. 10, 2005

(65) Prior Publication Data

US 2006/0152999 A1 Jul. 13, 2006

(51) Int. Cl.
*B01F 11/00* (2006.01)
(52) U.S. Cl. .................... 366/197; 366/343
(58) Field of Classification Search ........... 366/120, 366/332, 343, 197, 198, 206, 207; 422/100
See application file for complete search history.

(56) References Cited

U.S. PATENT DOCUMENTS

| | | | | |
|---|---|---|---|---|
| 2,615,692 A | * | 10/1952 | Muller | 366/273 |
| 2,737,373 A | * | 3/1956 | Kinley | 416/3 |
| 4,352,300 A | * | 10/1982 | Esch | 74/22 R |
| 4,720,374 A | | 1/1988 | Ramachandran | 422/310 |
| 5,215,376 A | * | 6/1993 | Schulte et al. | 366/348 |
| 5,413,770 A | | 5/1995 | Sakaguchi et al. | 422/255 |
| 5,443,791 A | * | 8/1995 | Cathcart et al. | 422/65 |
| 5,452,619 A | * | 9/1995 | Kawanabe et al. | 73/864.01 |
| 5,482,863 A | * | 1/1996 | Knobel | 436/54 |
| 5,824,276 A | | 10/1998 | Janssen et al. | 422/292 |
| 5,988,869 A | | 11/1999 | Davidson et al. | 366/208 |
| 6,059,446 A | | 5/2000 | Dschida | 366/215 |
| 6,322,243 B1 | | 11/2001 | Bull | 366/208 |
| 6,382,827 B1 | | 5/2002 | Gebrian | 366/274 |
| 6,390,660 B1 | | 5/2002 | Colin | 366/116 |
| 6,467,946 B1 | | 10/2002 | Gebrian | 366/273 |
| 6,808,304 B2 | | 10/2004 | Gebrian et al. | 366/110 |
| 6,880,384 B2 | | 4/2005 | Hvidtfeldt et al. | 73/64.56 |

* cited by examiner

*Primary Examiner*—David Sorkin
(74) *Attorney, Agent, or Firm*—Leland K. Jordan

(57) ABSTRACT

A method for rapidly and uniformly mixing solutions within a biochemical analyzer by rapidly and repeatedly moving a sampling probe in a two-dimensional boomerang-curved pattern within the solution.

5 Claims, 20 Drawing Sheets

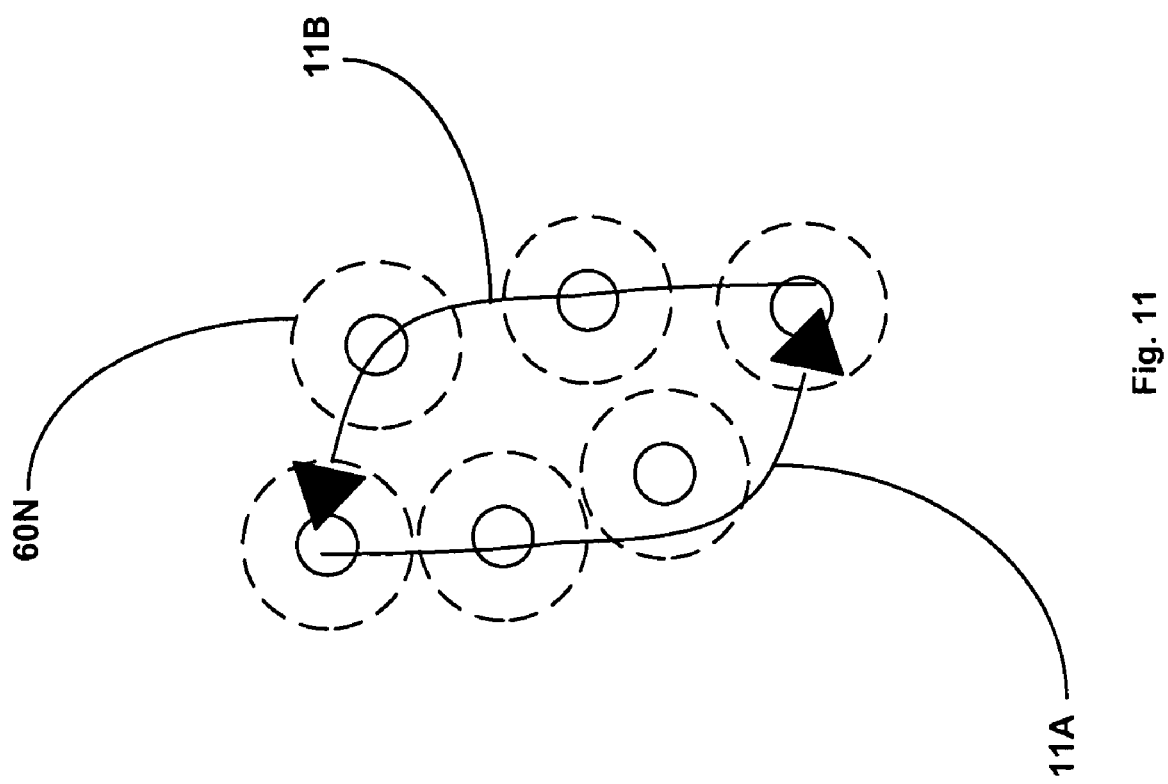

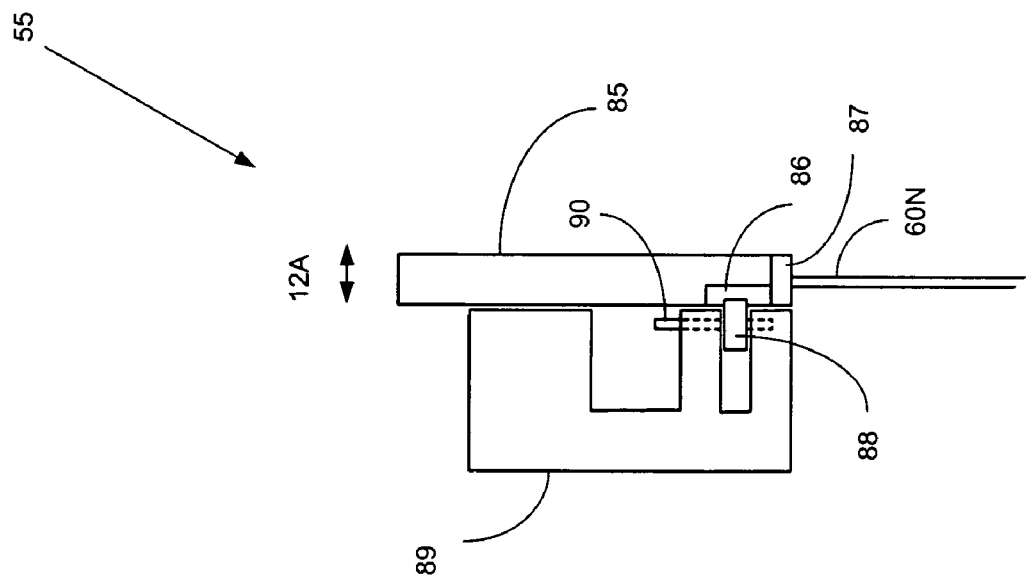

US 7,258,480 B2

APPARATUS FOR MIXING LIQUID SAMPLES USING A TWO DIMENSIONAL STIRRING PATTERN

FIELD OF THE INVENTION

The present invention relates to a method and apparatus for uniformly mixing liquid samples, reagents, or other solutions in a container. In particular, the present invention provides a method for rapidly and uniformly mixing a liquid solution by repeatedly moving a sampling probe needle in a two-dimensional curved pattern within the solution.

BACKGROUND OF THE INVENTION

Various types of analytical tests related to patient diagnosis and therapy can be performed by analysis of a liquid sample taken from a patient's infections, bodily fluids or abscesses. These assays are typically conducted with automated clinical analyzers onto which tubes or vials containing patient samples have been loaded. The analyzer extracts liquid sample from the vial and combines the sample with various reagents in special reaction cuvettes or tubes. Usually the sample-reagent solution is incubated or otherwise processed before being analyzed. Analytical measurements are often performed using a beam of interrogating radiation interacting with the sample-reagent combination, for example turbidimetric, fluorometric, absorption readings or the like. The measurements allow determination of endpoint or rate values from which an amount of analyte related to the health of the patient may be determined using well-known calibration techniques.

Clinical analyzers employ many different processes to identify analytes and throughout these processes, patient liquid samples, and samples in combination with various other liquids like reagents or diluents or re-hydrated compositions, are frequently required to be mixed to a high degree of uniformity. Due to increasing pressures on clinical laboratories to increase analytical sensitivity, there continues to be a need for improvements in the overall processing efficiency of clinical analyzers. In particular, sample analysis continuously needs to be more effective in terms of increasing assay throughput, producing a demand for sample-reagent mixers that mix a liquid solution to a high degree of uniformity at very high speed, without unduly increasing analyzer cost or requiring a disproportional amount of space.

Various methods have historically been implemented to provide a uniform sample solution mixture, including agitation, mixing, ball milling, etc. One popular approach involves using a pipette to alternately aspirate and release a portion of liquid solution within a liquid container. Magnetic mixing, in which a vortex mixing action is introduced into a solution of liquid sample and liquid or non-dissolving reagents has also been particularly useful in clinical and laboratory devices. Typical of such mixing is disclosed in U.S. Pat. No. 6,382,827 wherein a liquid solution in a liquid container is mixed by causing a freely disposed, spherical mixing member to rapidly oscillate within the solution in a generally circular pattern within the container. The spherical mixing member is caused to rapidly move within the solution by revolving a magnetic field at high speed in a generally circular pattern in proximity to the liquid container. Magnetic forces acting upon the magnetic mixing member cause it to generate a mixing motion within the liquid solution.

Ultrasonic mixing techniques like described in U.S. Pat. No. 4,720,374 employ ultrasonic energy applied from the exterior of the package and coupled into a reaction compartment so that a solid tablet of material within the compartment is dissolved or so that liquids contained therein are uniformly mixed. The container may include an array of sonication-improving projections mounted therein and spaced from each other to provide recirculating channels which communicate with both the tablet-receiving recess and the remainder of the volume of the container such that, in use, the projections act to confine a tableted material within a relatively high ultrasonic energy zone and simultaneously permit a flow of hydrating liquid from the high energy zone through the channels thereby to rapidly effect the dissolution of the tableted material.

U.S. Pat. No. 6,382,827 discloses a method for mixing a liquid solution contained in a liquid container by causing a freely disposed, spherical mixing member to rapidly oscillate within the solution in a generally circular pattern within the container. The spherical mixing member is caused to rapidly move within the solution by revolving a magnetic field at high speed in a generally circular pattern in proximity to the liquid container. Magnetic forces acting upon the magnetic mixing member cause it to generate a mixing motion within the liquid solution.

U.S. Pat. No. 5,824,276 discloses a method for cleaning contact lens by applying a solution flow in an oscillatory fashion, so that the lens moves up and down within a container but does not contact the container for an extended time period. The method includes suspending the article in a solution within a container such that the article does not experience substantial or extended contact with the container interior. A predetermined flow of solution is passed into the container, thereby providing an upward force which, in conjunction with the buoyancy force, overcomes the downward gravitational force on the article, when the article is more dense than the solution. Alternatively, if the article has a lower density than the treatment solution, the flow is generated at the top of the container, to produce a substantially steady state effect.

Accordingly, from a study of the different approaches taken in the prior art to the problems encountered with quickly mixing small volume solutions taken with the challenges of minimizing the cost and physical size of a mixer, there is a need for an improved approach to the design of a simplified, space-efficient liquid sample and or sample-reagent mixer. In particular, there is a continuing need for improved sample-reagent solution mixer which provides high speed and uniform mixing of solutions contained in tubes. There is an even further need for a method for uniform high-speed mixing having a mixing motion that is provided by the same probe that is used to aspirate and dispense reagent into the solution.

SUMMARY OF THE INVENTION

The principal object of the invention is to provide an improved mixing device for rapidly and uniformly mixing solutions within a biochemical analyzer by rapidly and repeatedly moving a sampling probe needle in a two-dimensional generally parabolic pattern within the solution. The sampling probe needle is attached to a moveable arm and the mixer reciprocates the moveable arm in a first direction and also reciprocates the arm in a second direction perpendicular to the first direction, so that the probe needle is moved in a generally parabolic pattern. In an exemplary embodiment, the probe needle is attached to a moveable arm having a protruding foot with a vertical roller pin in contact with a roller bearing. The moveable arm is vibrated by an alternating electromagnet in a first direction causing the roller pin to roll along the circumference of the roller bearing and the arm to move side-to-side in a in a second direction, generally perpendicular to the first direction. Varying the magnitude of movement of the moveable arm, in combination with adjusting the diameters of roller pin and roller bearing, produces a generally parabolic or generally "boomerang-shaped" generally ellipsoidal mixing pattern of the probe needle that has been found to be surprisingly efficient in time and effective in mixing uniformity. In one embodiment, the generally "boomerang-shaped" mixing pattern has a first dimension in said first direction and a second dimension in said second direction wherein the first dimension is about one-half as large as the second dimension.

BRIEF DESCRIPTION OF THE DRAWINGS

The invention will be more fully understood from the following detailed description thereof taken in connection with the accompanying drawings which form a part of this application and in which:

FIG. 11 is an enlarged diagram illustrating a first mixing pattern of motion generated by the roller mixing assembly exemplary of the present invention;

FIG. 12 is a side elevation view of the roller mixing assembly exemplary of the present invention;

DETAILED DESCRIPTION OF THE INVENTION

Figure 1:
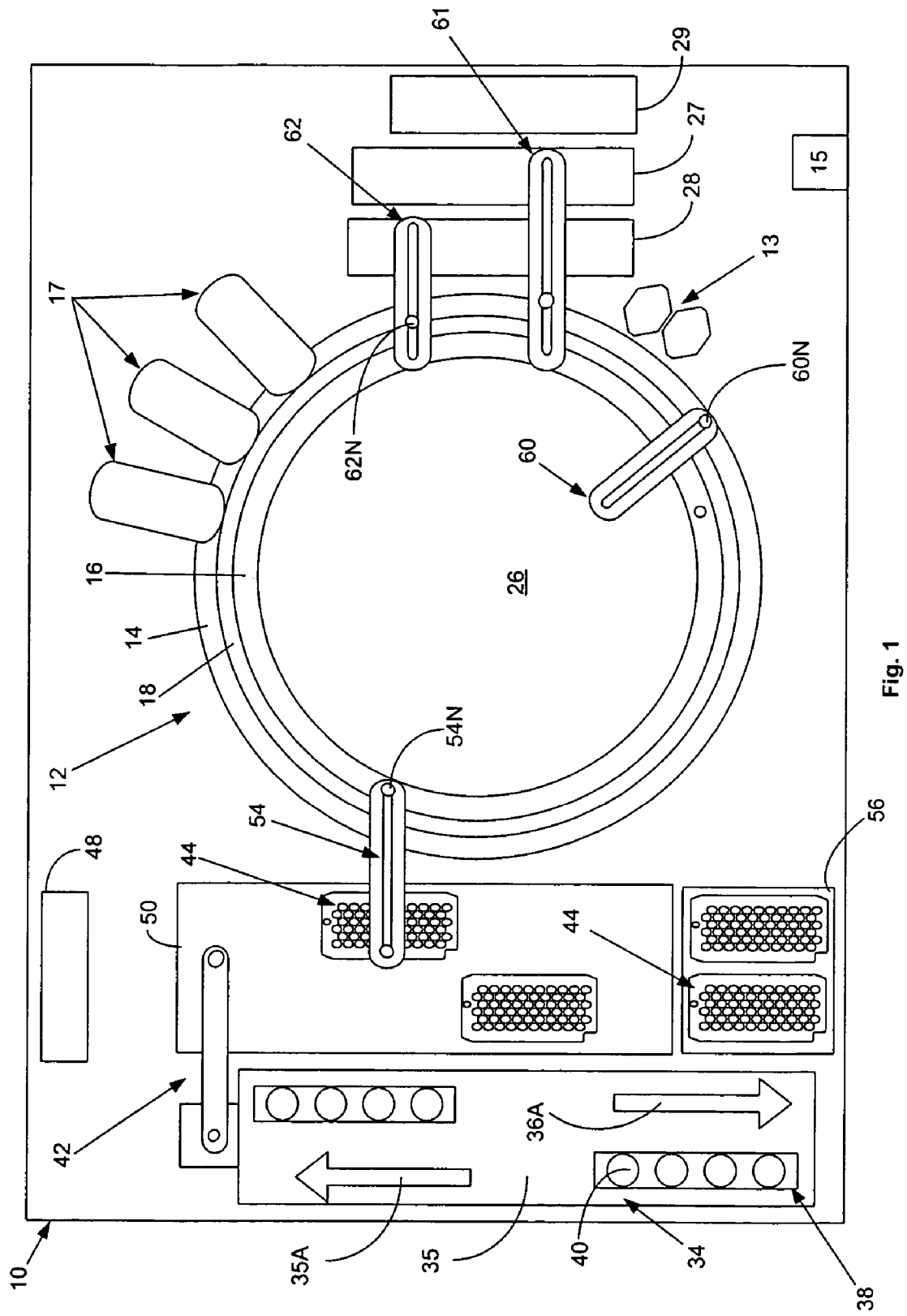
FIG. 1 is a schematic plan view of an automated analyzer adapted to perform the present invention.
Figure 2:
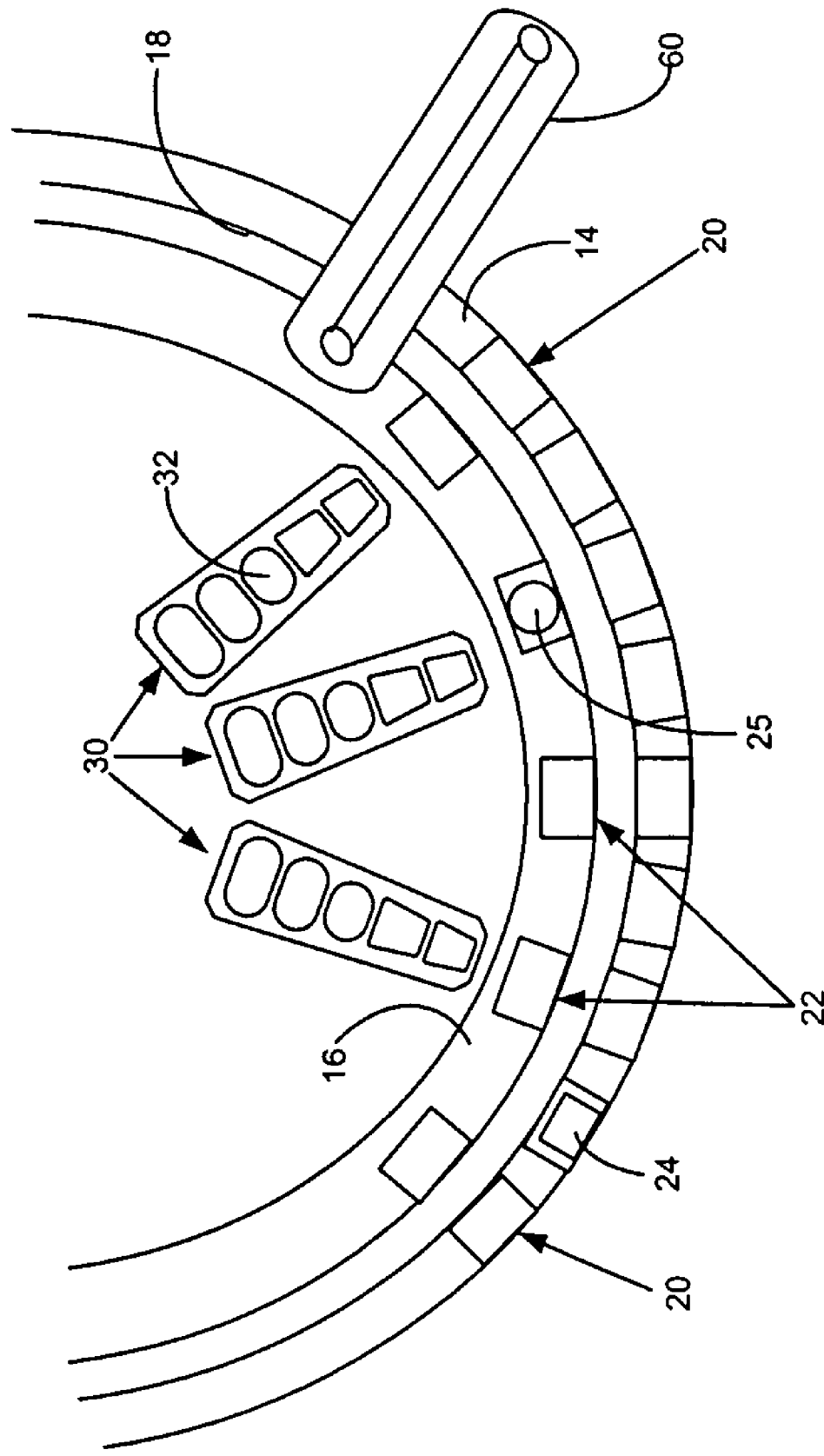
FIG. 2 is an enlarged schematic plan view of a portion of the analyzer of FIG. 1.
Figure 2A:
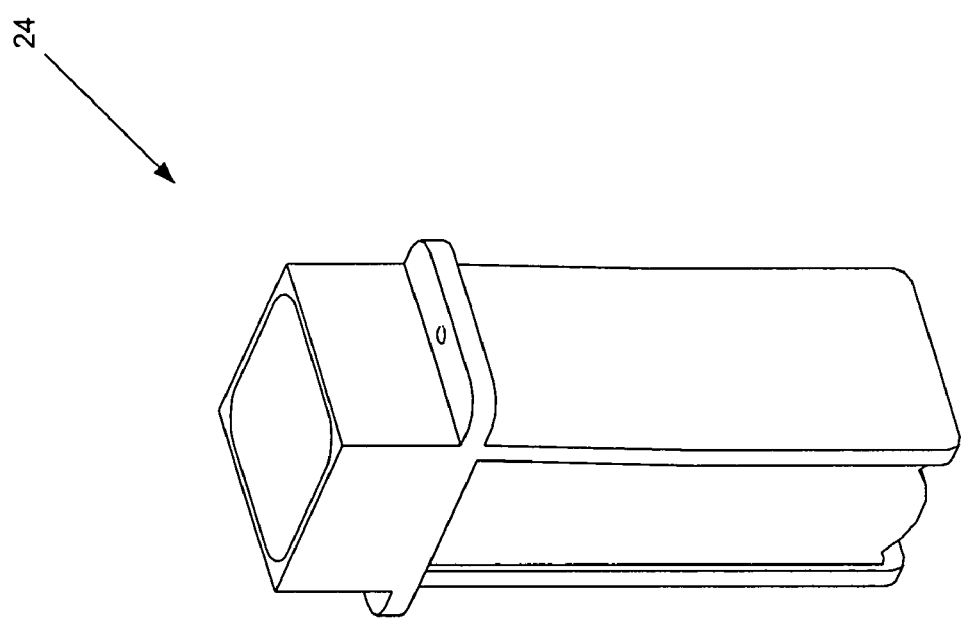
FIG. 2A is perspective view of a reaction cuvette useful in operating the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer carousel 14 having cuvette ports 20 formed therein and an inner carousel 16 having vessel ports 22 formed therein, the outer carousel 14 and inner carousel 16 being separated by a open groove 18. Cuvette ports 20 are adapted to receive a plurality of reaction cuvettes 24, like seen in FIG. 2A, that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which reaction carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

As seen in FIG. 1, a bidirectional incoming and outgoing sample fluid tube transport system 34 comprises a mechanism for transporting sample fluid tube racks 38 containing open or closed sample fluid containers such as sample fluid tubes 40 from a rack input load position at a first end of the input lane 35 to the second end of input lane 35 as indicated by open arrow 35A. Liquid specimens contained in sample tubes 40 are identified by reading bar coded indicia placed thereon using a conventional bar code reader to determine, among other items, a patient's identity, tests to be performed, if a sample aliquot is to be retained within analyzer 10 and if so, for what period of time. It is also common practice to place bar coded indicia on sample tube racks 38 and employ a large number of bar code readers installed throughout analyzer 10 to ascertain, control and track the location of sample tubes 40 and sample tube racks 38.

Figure 3:
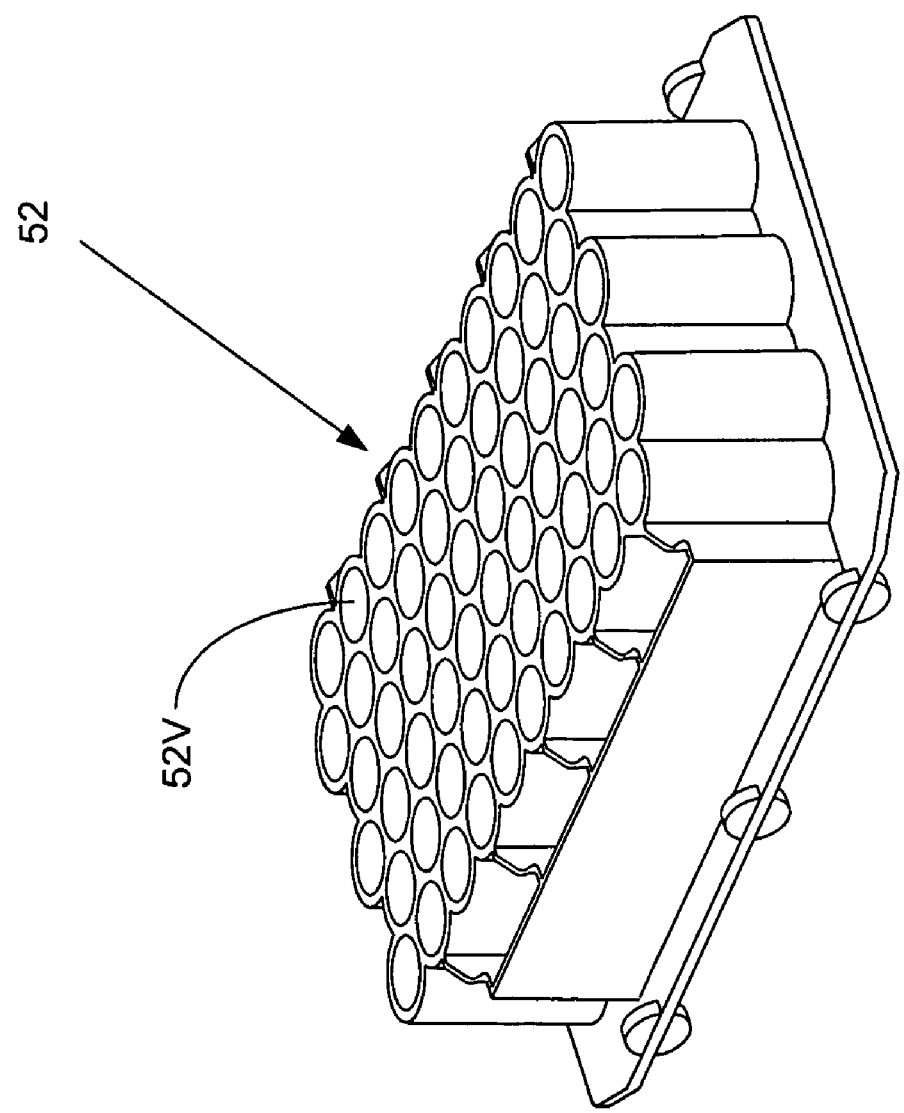
FIG. 3 is perspective view of an aliquot vessel array useful in the analyzer of FIG. 1.
Figure 4:
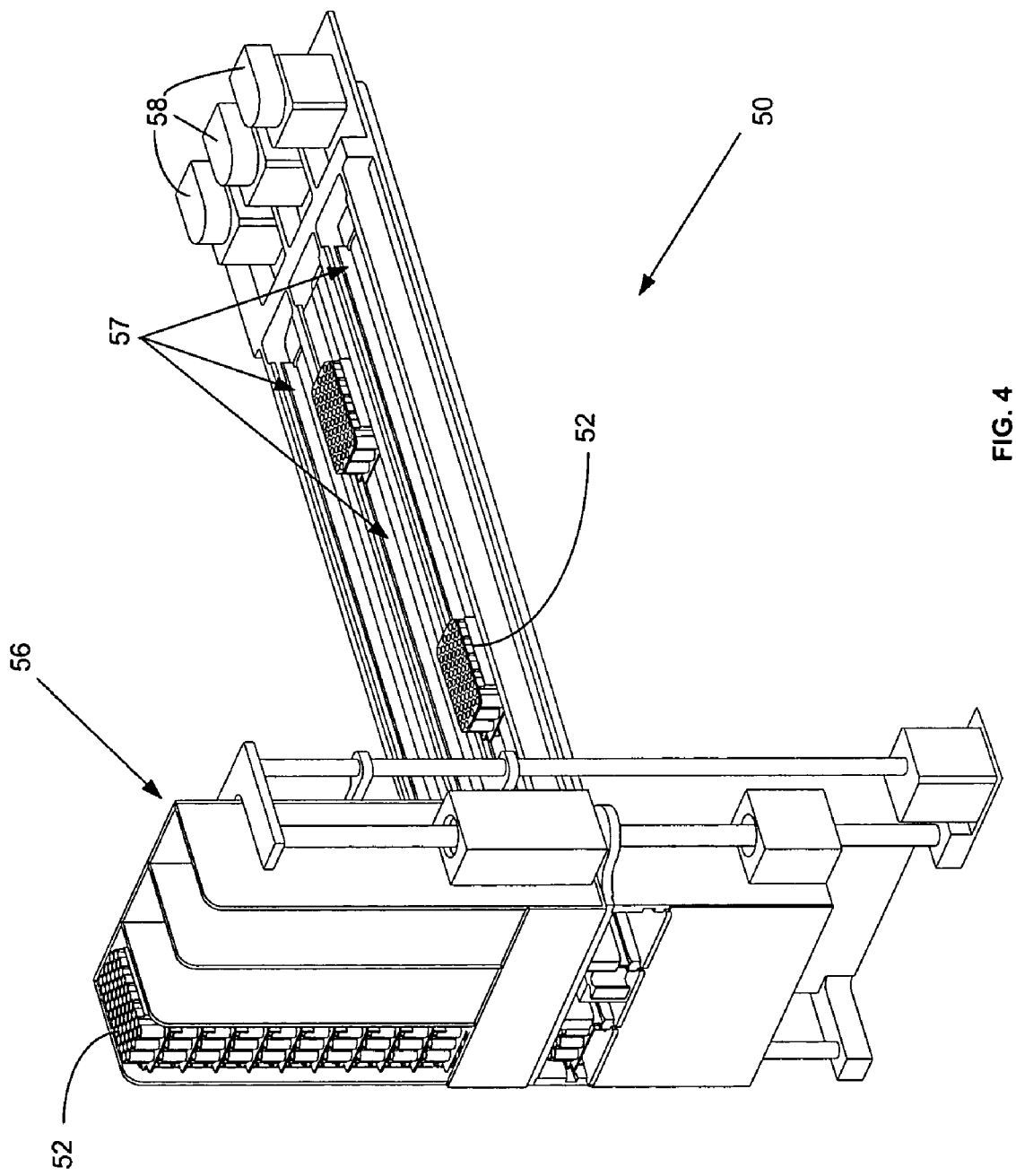
FIG. 4 is a perspective view of an aliquot vessel array storage and handling unit of the analyzer of FIG. 1.

A conventional liquid sampling probe 42 is located proximate the second end of the input lane 35 and is operable to aspirate aliquot portions of sample fluid from sample fluid tubes 40 and to dispense an aliquot portion of the sample fluid into one or more of a plurality of vessels 52V in aliquot vessel array 44, seen in FIG. 3, depending on the quantity of sample fluid required to perform the requisite assays and to provide for a sample fluid aliquot to be retained by analyzer 10 within an environmental chamber 48. After sample fluid is aspirated from all sample fluid tubes 40 on a rack 38 and dispensed into aliquot vessels 52V maintained in an aliquot vessel array storage and transport system 50 seen in FIG. 4, rack 38 may be moved, as indicated by open arrow 36A, to a front area of analyzer 10 accessible to an operator so that racks 38 may be unloaded from analyzer 10.

Aliquot vessel array transport system 50 comprises an aliquot vessel array storage and dispensing module 56 and a number of linear drive motors 58 adapted to bi-directionally translate aliquot vessel arrays 52 within a number of aliquot vessel array tracks 57 below a sample aspiration needle probe 54 and roller mixing assembly 55, described hereinafter and exemplary of the present invention, located proximate reaction carousel 12. Sample aspiration probe 54 is controlled by computer 15 and is adapted to aspirate a controlled amount of sample from individual vessels 52V positioned at a sampling location within a track 57 and is then shuttled to a dispensing location where an appropriate amount of aspirated sample is dispensed into one or more cuvettes 24 for testing by analyzer 10 for one or more analytes. After sample has been dispensed into reaction cuvettes 24, conventional transfer means move aliquot vessel arrays 52 as required between aliquot vessel array transport system 50, environmental chamber 48 and a disposal area, not shown.

Figure 5:
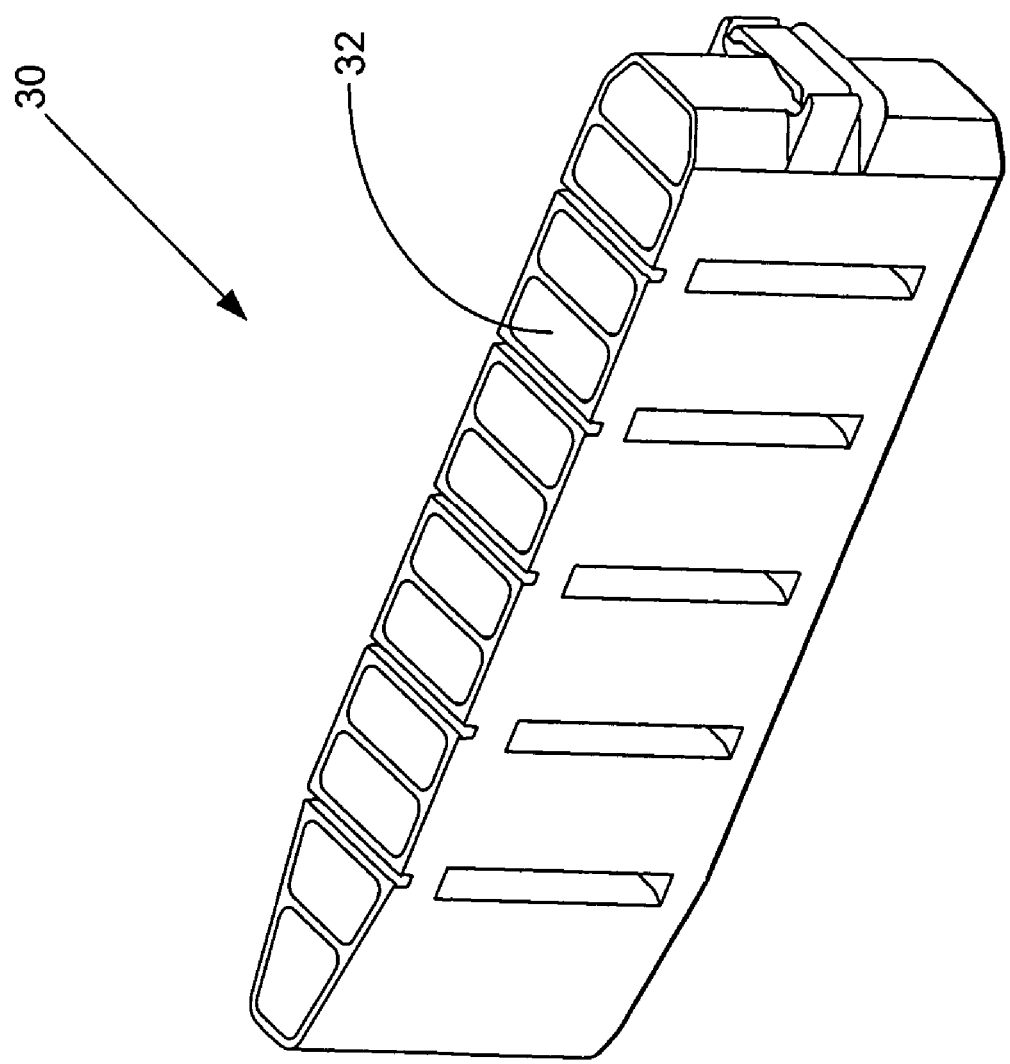
FIG. 5 is perspective view of a reagent cartridge useful in operating the analyzer of FIG. 1.
Figure 6:
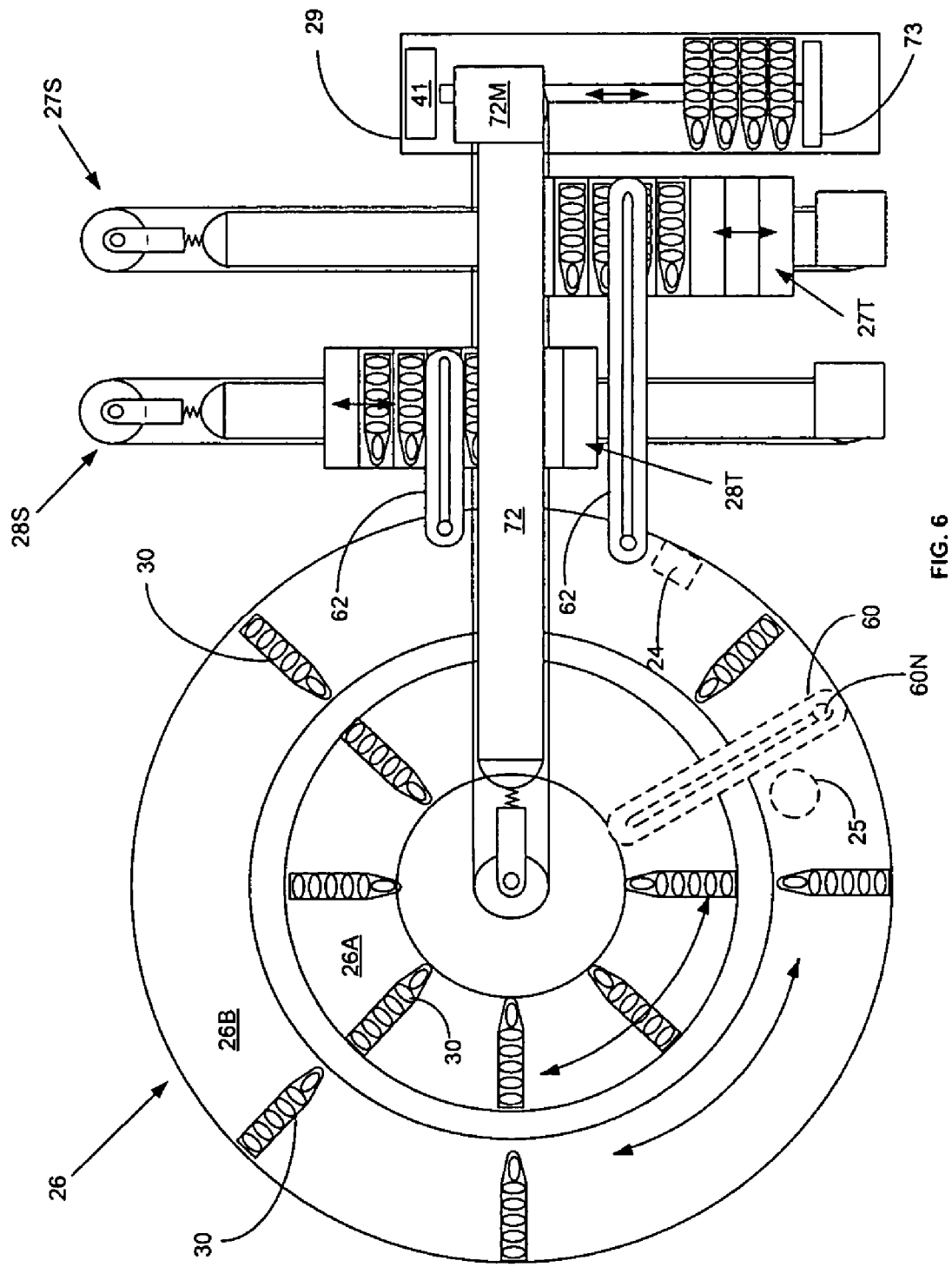
FIG. 6 is a top plan view of a reagent cartridge management system useful in operating the analyzer of FIG. 1.

Temperature-controlled storage areas or servers 26, 27 and 28 inventory a plurality of multi-compartment elongate reagent cartridges 30, like that illustrated in FIG. 5 and described in co-pending application Ser. No.: 09/949,132 assigned to the assignee of the present invention, containing reagents in wells 32 as necessary to perform a number of different assays. As described later in conjunction with FIG. 6, server 26 comprises a first carousel 26A in which reagent cartridges 30 may be inventoried until translated to a second carousel 26B for access by a reagent aspiration probe 60 and roller mixing assembly 55 exemplary of the present invention. FIG. 6 shows an advantageous embodiment in which carousel 26A and carousel 26B are circular and concentric, the first carousel 26A being inwards of the second carousel 26B. Reagent containers 30 may be loaded by placing such containers 30 into a loading tray 29 adapted to automatically translate containers 30 to a shuttling position described later.

Additional reagent aspiration needle probe 62 is also associated with a roller mixing assembly 55 like that associated with aspiration probe 60 are independently mounted and translatable between servers 27 and 28, respectively and outer cuvette carousel 14. Probe 62 comprises conventional mechanisms for aspirating reagents required to conduct specified assays at a reagenting location from wells 32 in appropriate reagent cartridges 30, probe 62 subsequently being shuttled to a dispensing location where reagents are dispensed into cuvettes 24.

Figure 7:
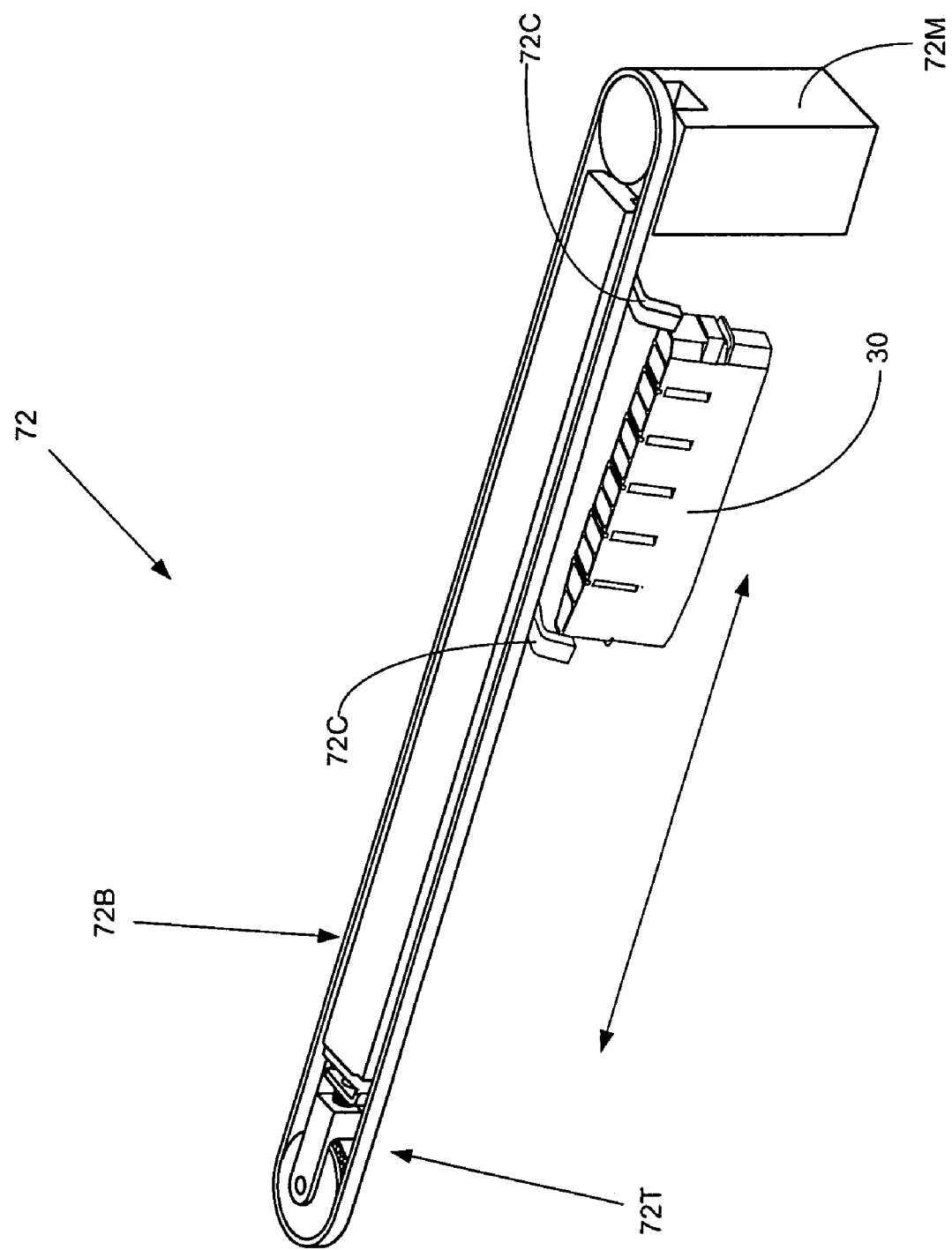
FIG. 7 is perspective view of a reagent cartridge useful in the reagent cartridge management system of FIG. 6.

FIG. 6, taken with FIG. 7, illustrates a single, bidirectional carrier shuttle 72 adapted to remove reagent cartridges 30 from loading tray 29 having a motorized rake 73 that automatically locates reagent cartridges 30 at a shuttling position beneath shuttle 72. Cartridges 30 are identified by the type of reagent solution contained therein using conventional barcode-like indicia and a bar-code-reader 41 proximate loading tray 29. Computer 15 is programmed to track the location of each and every reagent cartridge 30 within analyzer 10. Shuttle 72 is further adapted to dispose a reagent container 30 into slots in at least one slotted reagent container tray 27T or 28T within at least one reagent storage area 27 or 28, respectively. In a similar fashion, shuttle 72 is further adapted to remove reagent containers 30 from reagent container trays 27T and 28T and to dispose such reagent containers 30 into either of two concentric reagent carousels 26A and 26B within reagent storage area 26. Shuttle 72 is also adapted to move reagent containers 30 between the two concentric reagent carousels 26A and 26B. As indicated by the double-headed arc-shaped arrows, reagent carousel 26A may be rotated in both directions so as to place any particular one of the reagent containers 30 disposed thereon beneath reagent aspiration probe 60. Any one of the reagent containers 30 disposed in reagent container trays 27T and 28T may be located at a loading position beneath reagent container shuttle 72 or at a reagent aspiration location beneath aspiration and dispensing probe 62, respectively, by reagent container shuttles 27S and 28S within reagent storage areas 27 and 28, respectively. Reagent container shuttles 27S and 28S are similar in design to reagent container shuttle 72 seen in FIG. 7. Reaction cuvettes 24 supported in outer carousel 14 and reaction vessels 25 supported in inner carousel 16 are shown in dashed lines to indicate that they are positioned below the surface of carousel 26.

Carrier shuttle 72 seen in FIG. 7 is adapted to automatically compensate for unknown changes in length of a belt 72B driven by motor 72M by an automated tensioner 72T like described in co-pending U.S. Pat. Ser. No. 10/623,311 and assigned to the assignee of the present invention, and adapted to maintain a constant tension on the belt 72B regardless of rapid changes in its driving direction so that reagent containers 30 attached thereto by clamps 72C may be accurately positioned along the direction of belt 72B, as indicated by the double-ended arrow, and disposed at their shuttling location beneath reagent container shuttle 72 or within storage areas 26, 27 or 28 as belt 72B wears. Reagent container shuttles 27S and 28S are similar in design to one another and include a reagent container tray 28T secured to one leg of a belt so that tray 28T is free to be driven to and from along the direction of by the double-ended arrow. Consequently, reagent containers 30 within slots in tray 28T may be automatically positioned at a shuttling location beneath container shuttle 72.

Figure 8:
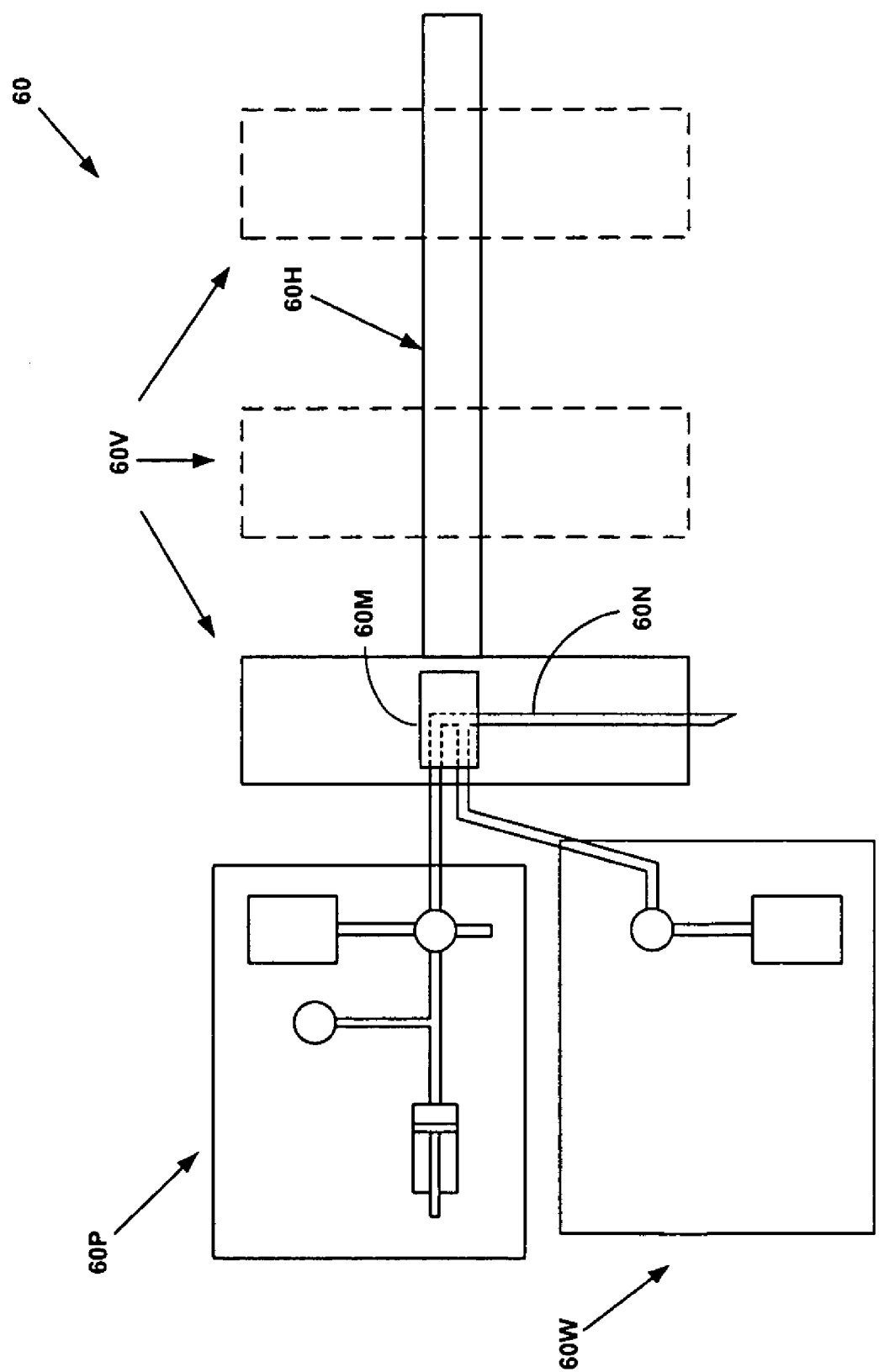
FIG. 8 is a schematic view of a liquid aspiration and dispensing system useful in the analyzer of FIG. 1.

Aspiration probe 60 useful in performing the present invention may be seen in FIG. 8 as comprising a Horizontal Drive component 60H, a Vertical Drive component 60V, a Wash Module component 60W, a Pump Module component 60P, an aspiration and dispensing probe needle 60N, and a Wash Manifold component 60M having the primary functions described in Table 1. Components of the Wash Module component 60W and Pump Module component 60P unidentified in FIG. 9 will be described later. Horizontal Drive component 60H and Vertical Drive component 60V are typically computer controlled stepper motors or linear actuators and are controlled by computer 15 for providing precisely controlled movements of the Horizontal Drive component 60H and Vertical Drive component 60V.

TABLE 1

| Module | Primary Functions |
| --- | --- |
| Horizontal Drive 60H | Position the Vertical Drive 60V over reagent cartridges 30 containing reagent liquids and carried in a vial rack 30A and over cuvettes 24 carried in ports 20. |
| Vertical Drive 60V | Drive probe 60N through the covering of a reagent cartridge 30. |
| Wash Module 60W | Remove contamination from needle 60N with liquid cleansing solutions. |
| Wash Manifold 60M | Connect needle 60N to Pump Module 60P |
| Pump Module 60P | Pump reagent liquids and sample fluids. |
| Needle 60N | Aspirate and dispense reagent liquids and sample fluids. |

Figure 9:
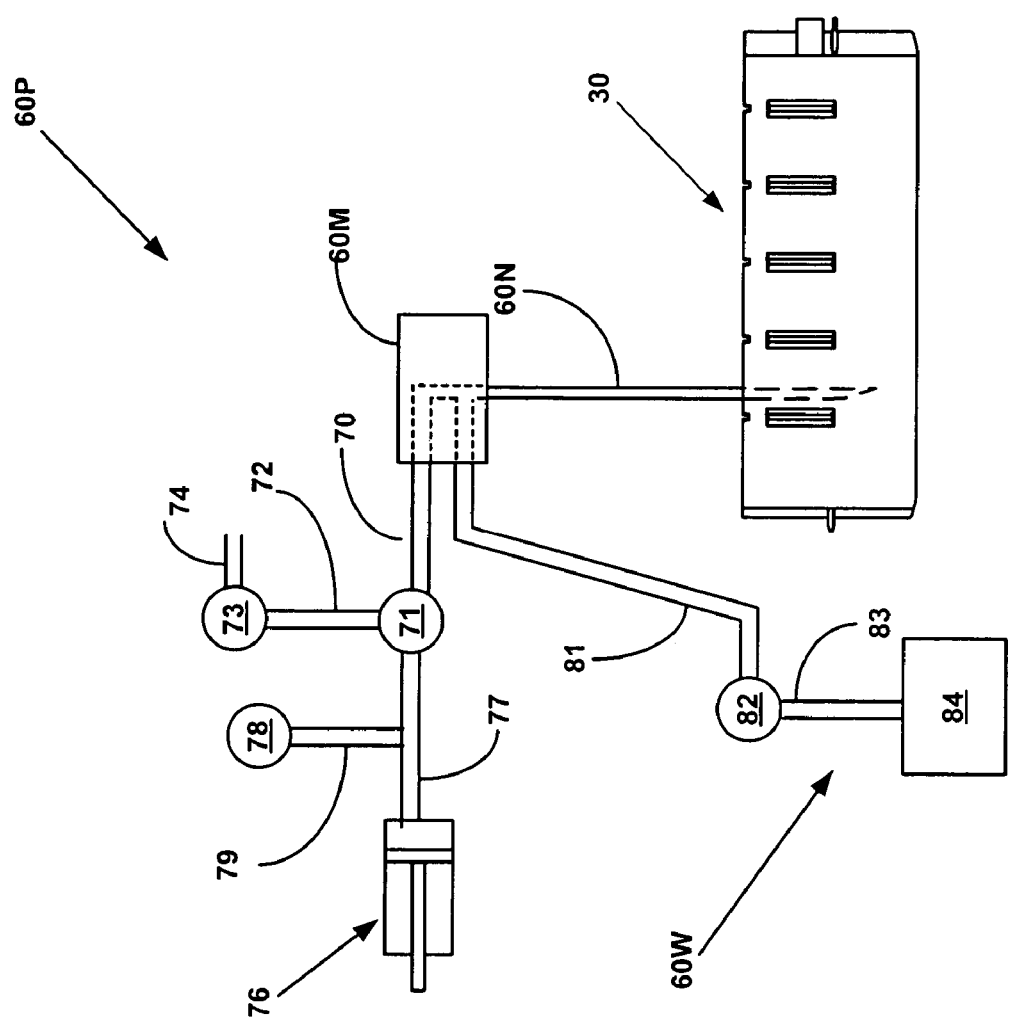
FIG. 9 is a schematic view of the liquid aspiration and dispensing system of FIG. 8 aspirating reagent from the reagent cartridge of FIG. 6.

FIG. 9 shows Pump Module 60P connected to conventional hollow, liquid-carrying probe-like needle 60N having conventionally defined interior and exterior surfaces and supported by Wash Manifold 60M, the Wash Manifold 60M being connected by a hollow air tube 70 to a three-way valve 71. Probe needle 60N preferably has a tapered point designed to reduce friction when inserted through the covering of reagent cartridge 30 and may be connected to Wash Manifold 60M using any of several screw-like connectors, not shown, or alternately, permanently welded thereto. Valve 71 is operable to optionally connect air tube 70 to (1) a vent valve 73 connected to an atmospheric vent tube 74 or to (2) a piston-type syringe pump 76 by a hollow air tube 77. A conventional air pressure measuring transducer 78 is connected to air tube 77 between pump 76 and valve 71 by a hollow air tube 79.

FIG. 9 also illustrates probe needle 60N having punctured the covering of a reagent carrier 30 and positioned within a reagent liquid contained therein. Level sensing means, for example using well known capacitive signals, are may be advantageously employed in order to ensure that probe needle 60N is in fluid communication with the liquid. Piston 76 is activated and the distance it is moved is controlled by computer 15 so that a controlled volume of reagent liquid is withdrawn or aspirated into probe needle 60N. During this process, valve 71 is closed to vent tube 72, but is open to air tube 77 and air tube 70. Valve 71 is operable to optionally connect air tube 70 to a vent valve 73 connected to an atmospheric vent tube 74. FIG. 9 also shows Wash Manifold 60W as comprising a flush valve 82 connected to Wash Manifold 60W by a hollow liquid carrying tube 81. Flush valve 82 is operable to connect liquid carrying tube 81 to a pressurized rinse water source 84 by a hollow liquid tube 83. After aspiration of calibration or quality control liquid from reagent carrier 30 is completed, Wash Manifold 60M is raised by Vertical Drive 60V and positioned by Horizontal Drive 60H so that probe 60 may dispense calibration or quality control liquid into a cuvette 24 carried in port 20 in carousel 14 as illustrated in FIG. 10.

During operation of analyzer 10 using the devices illustrated in FIGS. 2-9, there are several instances when it is critical that liquids or solutions of one or more liquids be quickly and uniformly mixed producing a demand for a mixing device that mixes a liquid or liquid solution to a high degree of uniformity at very high speed, without unduly increasing analyzer cost or requiring a disproportional amount of space or a specialized mixing-only device. High speed mixing to obtain a uniformly dispersed solution might be required, for example:

1. After sample aspiration needle probe 60 extracts a first reagent from a first reagent cartridge 30 and dispenses reagent into a reaction cuvette 24, roller mixing assembly 55 may be operated to cause needle 60N to mix reagent and an optional chase or probe cleaning liquid;
2. Before sample aspiration needle probe 54 extracts sample from a vessel 52V in aliquot vessel array 44 and dispenses sample into a reaction cuvette 24, roller mixing assembly 55 may be operated to cause needle 54N to mix sample that has been retained in vessel 52V for an extended period of time waiting re-testing or additional testing;
3. Before sample aspiration needle probe 54 extracts sample from a vessel 52V in aliquot vessel array 44 and dispenses sample into a reaction cuvette 24, roller mixing assembly 55 may be operated to cause needle 60N to mix sample that has been diluted in vessel 52V; and,
4. After sample aspiration needle probe 54 extracts a second reagent from a first reagent cartridge 30 and dispenses reagent into reaction cuvette 24, roller mixing assembly 55 may be operated to cause needle 60N to mix reagent and an optional chase or probe cleaning liquid.
5. After sample aspiration needle probe 54 extracts sample from a vessel 52V in aliquot vessel array 44 and dispenses sample into a reaction cuvette 24, roller mixing assembly 55 may be operated to cause needle 60N to mix the sample with the reagent in the reaction cuvette 24.

Figure 10:
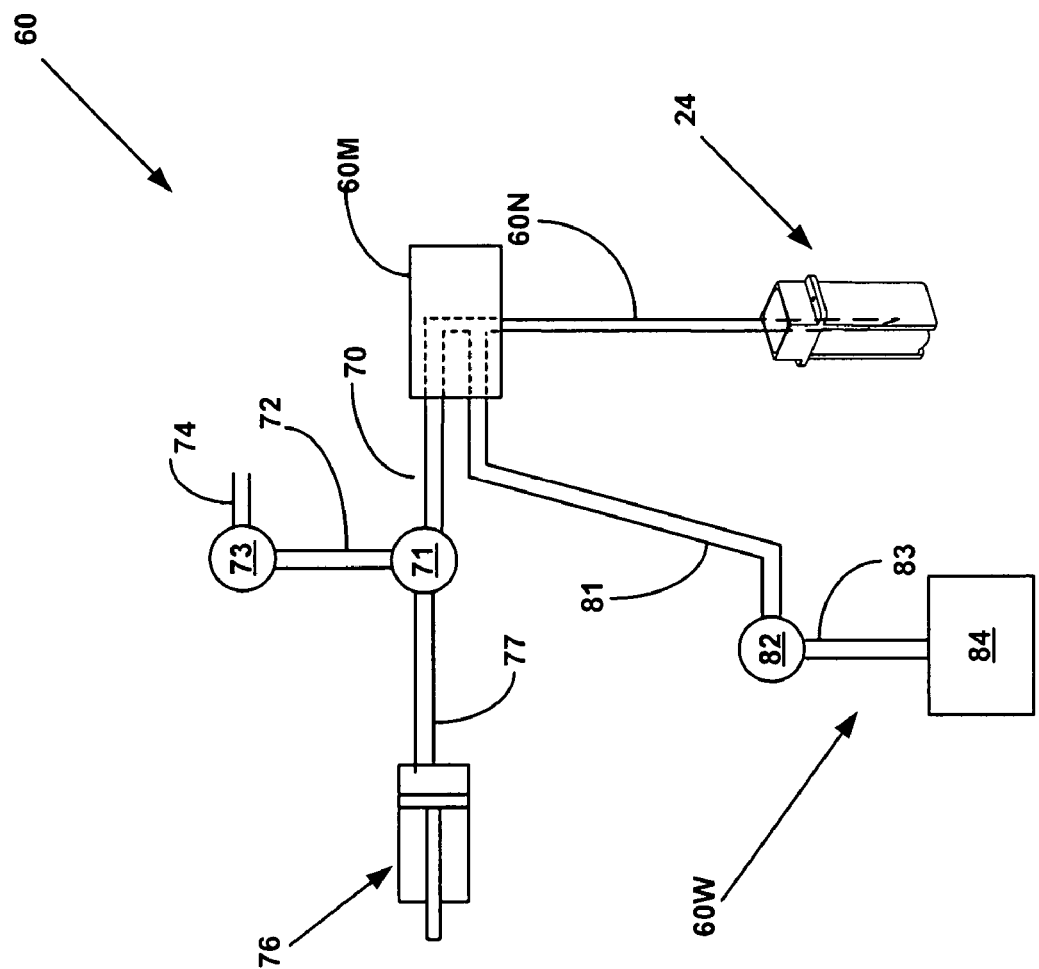
FIG. 10 is a schematic view of the liquid aspiration and dispensing system of FIG. 8 dispensing reagent into the reaction cuvette of FIG. 2A.

A key feature of the present invention is the discovery that an unexpectedly high degree of mixing uniformity may be achieved by using roller mixing assembly 55 to rapidly move probe needles 54N, 60N or 62N in a "boomerang-shaped" pattern within either the reagents in wells 32 prior to the reagent aspiration process illustrated in FIG. 9 or within sample retained in vessels 52V in aliquot vessel array 44, or within sample-reagent mixture in cuvette 24 after the dispensing process illustrated in FIG. 10.

Figure 11A:
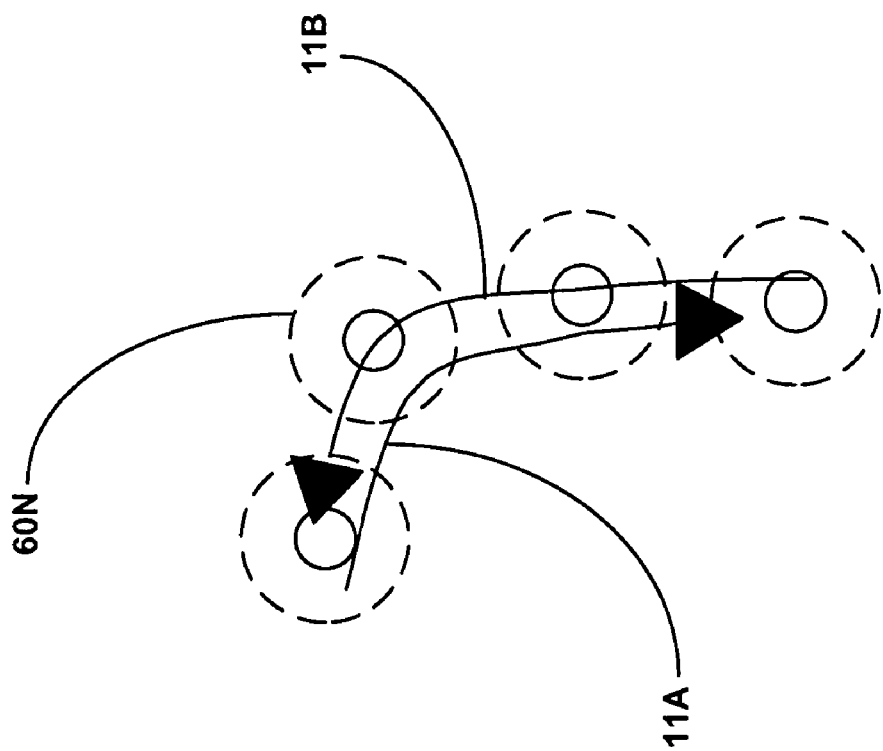
FIG. 11A is an enlarged diagram illustrating a second mixing pattern of motion generated by the roller mixing assembly exemplary of the present invention.
Figure 13:
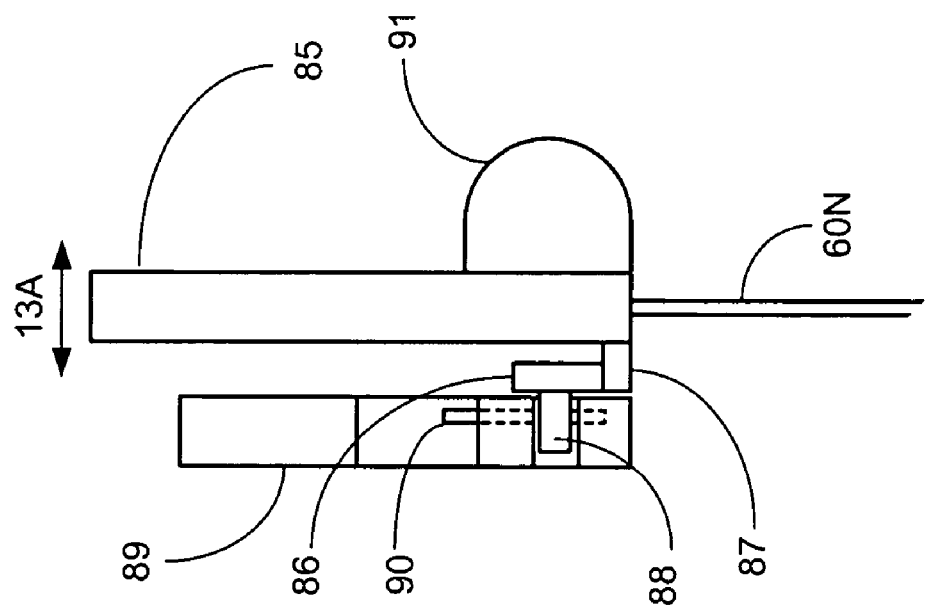
FIG. 13 is a front view of the roller mixing assembly exemplary of the present invention exemplary of the present invention.
Figure 14:
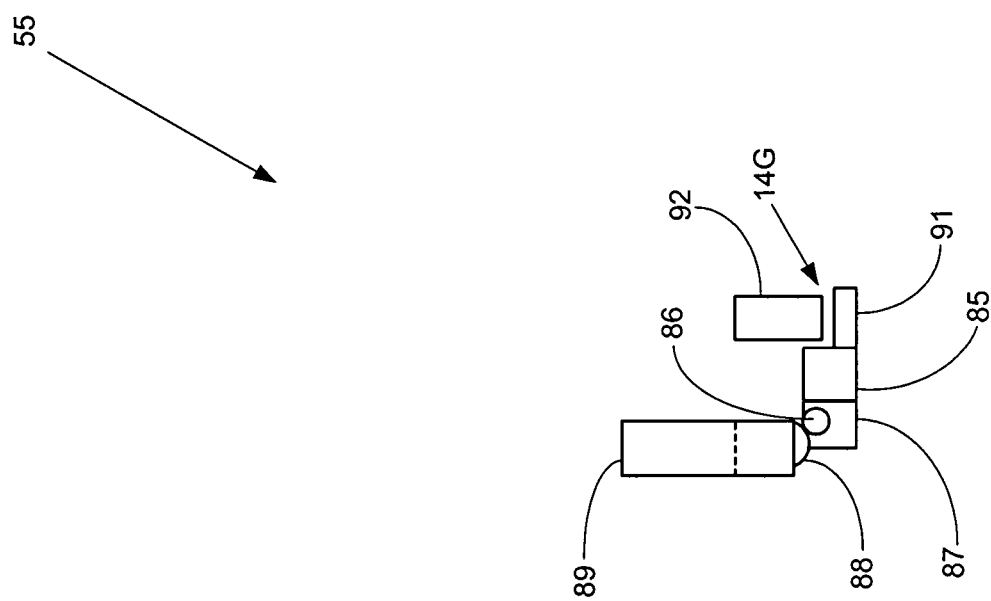
FIG. 14 is a top view of the roller mixing assembly exemplary of the present invention exemplary of the present invention.

The mixing action provided by the roller mixing assembly 55 exemplary of the present invention cycles probe needle 60N in a first mixing generally parabolic pattern like seen in FIG. 11 or in a second generally "boomerang-shaped" like seen in FIG. 11A in which needle probe 60N is moved along a path beginning at the tail of arrow 11A and following arrow 11A to it's point; at the point of arrow 11A, the movement of needle probe 60N is reversed and needle probe 60N is moved along a path beginning at the tail of arrow 11B and following arrow 11B to it's point. The tail of arrow 11A and the point of arrow 11B coincide and the point of arrow 11A the tail of arrow 11B coincide. Probe needle 60N is continuously moved in either the generally ellipsoidal pattern or in the "boomerang-shaped" pattern using roller mixing assembly 55 comprising a first means to provide reciprocating left-to-right movement and a second means to provide front-to-back reciprocating movement of the probe needle 60N, thereby producing a generally parabolic, FIG. 11, or "boomerang-shaped" mixing pattern, FIG. 11A. Conventional wisdom might employ two electromagnets to provide the two means for reciprocating needle 60N, it has been found to be much more cost effective to employ only one electromagnet coupled with a curved surface and with needle probe 60N as illustrated in FIGS. 12-14 to produce a generally ellipsoidal mixing pattern. In addition, a key advantage of the roller mixing assembly 55 over other mixing device design is the lack of motors and the use of a simple on-off signal, as opposed to a control system to maintain a motor speed), thereby reducing manufacturing cost and at the same time, producing a more reliable and durable mixing design. As discussed later, by changing the operating conditions of the mixer such as frequency and duty cycle, the boomerang pattern can be altered as shown in FIG. 11 and FIG. 11A. Clearly, probe needles 54N and 62N may also be moved in the same "boomerang-shaped" pattern by roller mixing assembly 55 in order to achieve high efficiency mixing.

FIG. 12 shows a front view of needle probe 60N depending from a protruding foot 87 of a moveable arm 85 of roller mixing assembly 55. The protruding foot 87 has a roller pin 86 extending vertically upwards and in contact with a curved surface provided by a roller bearing 88 mounted to a stationary block 89 using a pin 90. The needle probe 60N is attached to a moveable arm 85 having a protruding foot 87 with a vertical roller pin 86 in contact with a roller bearing 88. Roller bearing 88 is advantageously employed to provide a curved surface to provide side-to-side movement because such a bearing reduces friction and wear. However, any similar curved surface, for example a stationary pin or semi-circular surface with a circumference would suffice in providing the desired motion. The moveable arm 85 is vibrated by a conventional alternating electromagnet 92 and a ferromagnetic plate 91 in a first direction causing roller pin 86 to roll along the circumference of roller bearing 88 and arm 86 to move side-to-side in a in a second direction, perpendicular to the first direction. Varying the magnitude of movement of the moveable arm 86, in combination with adjusting the diameters of roller pin 86 and roller bearing 88, produces a "boomerang-shaped" mixing pattern of needle probe 60N that has been found to be surprisingly efficient in time and effective in mixing uniformity. In an exemplary embodiment, the "boomerang-shaped" mixing pattern has a first dimension in the first direction and a second dimension in the second direction wherein the first dimension is about one-half as large as the second dimension.

Moveable arm 85 is biased so that left-to-right movement a first distance, indicated in FIG. 12 by arrow 12A, forces roller pin 86 to roll along the outer circumference of roller bearing 88, thereby causing arm 85 to also move a second distance in a direction perpendicular to the plane of FIG. 12. This movement in the second direction of arm 85, perpendicular to the first direction is illustrated by arrow 13A in FIG. 13, a right side view of roller mixing assembly 55, in which a ferromagnetic plate 91 is shown attached to arm 85. Plate 91 is caused to vibrate perpendicularly to the plane of FIG. 13 by an alternating electromagnet 92, seen in FIG. 14. Varying the phase of alternating electric current supplied to electromagnet 92 causes plate 91 and arm 85 to oscillate in a direction perpendicular to the plane of FIG. 13, forcing roller pin 86 to roll along the outer circumference of roller bearing 88, thereby causing arm 85 to move sidewise in the direction of double-headed arrow 13A. The dimension of movement in the second direction is generally larger than the dimension of movement in the first direction, and in an exemplary embodiment is generally twice as large as the dimension of movement in the first direction. A close examination of FIGS. 12-14 reveals how needle probe 60N may be continuously moved in the "boomerang-shaped" pattern of FIG. 11 using roller mixing assembly 55. It is clear that varying the magnitude of movement of plate 91 and arm 85, in combination with modifying the diameters of roller pin 86 and roller bearing 88, can alter the dimensions of the generally ellipsoidal patter seen in FIG. 11 or the "boomerang-shaped" pattern seen in FIG. 11A, however the overall shape of such a pattern will remain approximately similar.

The dimension of movement in the second direction is generally twice as large as the dimension of movement in the first direction. A close examination of FIGS. 12-14 reveals how needle probe 60N may be continuously moved in the "boomerang-shaped" pattern of FIG. 11 using roller mixing assembly 55. It is clear that varying the magnitude of movement of plate 91 and arm 85, in combination with modifying the diameters of roller pin 86 and roller bearing 88, can alter the dimensions of the generally ellipsoidal patter seen in FIG. 11 or the "boomerang-shaped" pattern seen in FIG. 11A, however the overall shape of such a pattern will remain approximately similar.

Figure 15:
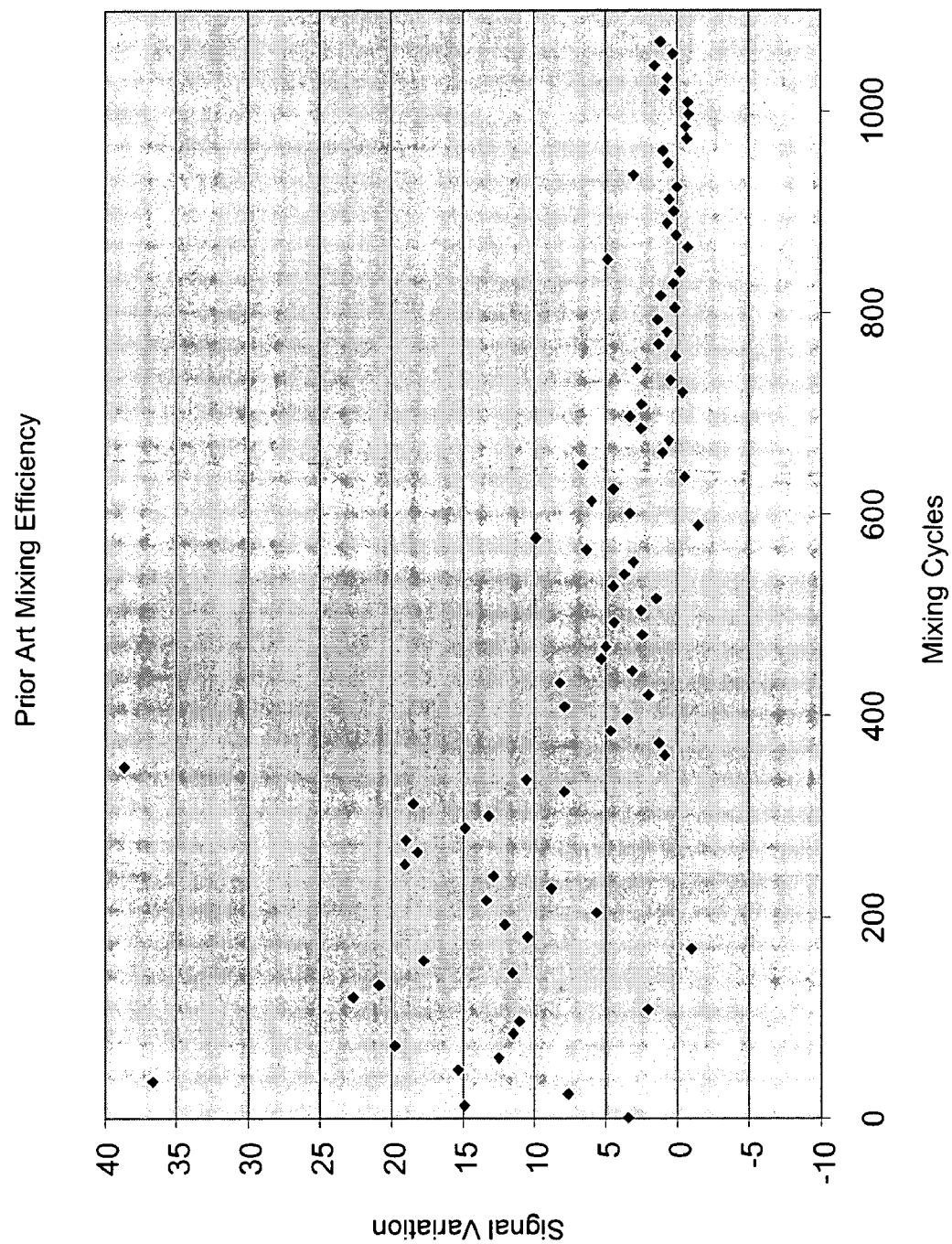
FIG. 15 is a chart illustrating the mixing effectiveness of a popular prior art mixing patterns; and, FIG. 16 is a first chart illustrating the mixing effectiveness of the roller mixing assembly exemplary of the present invention.
Figure 16:
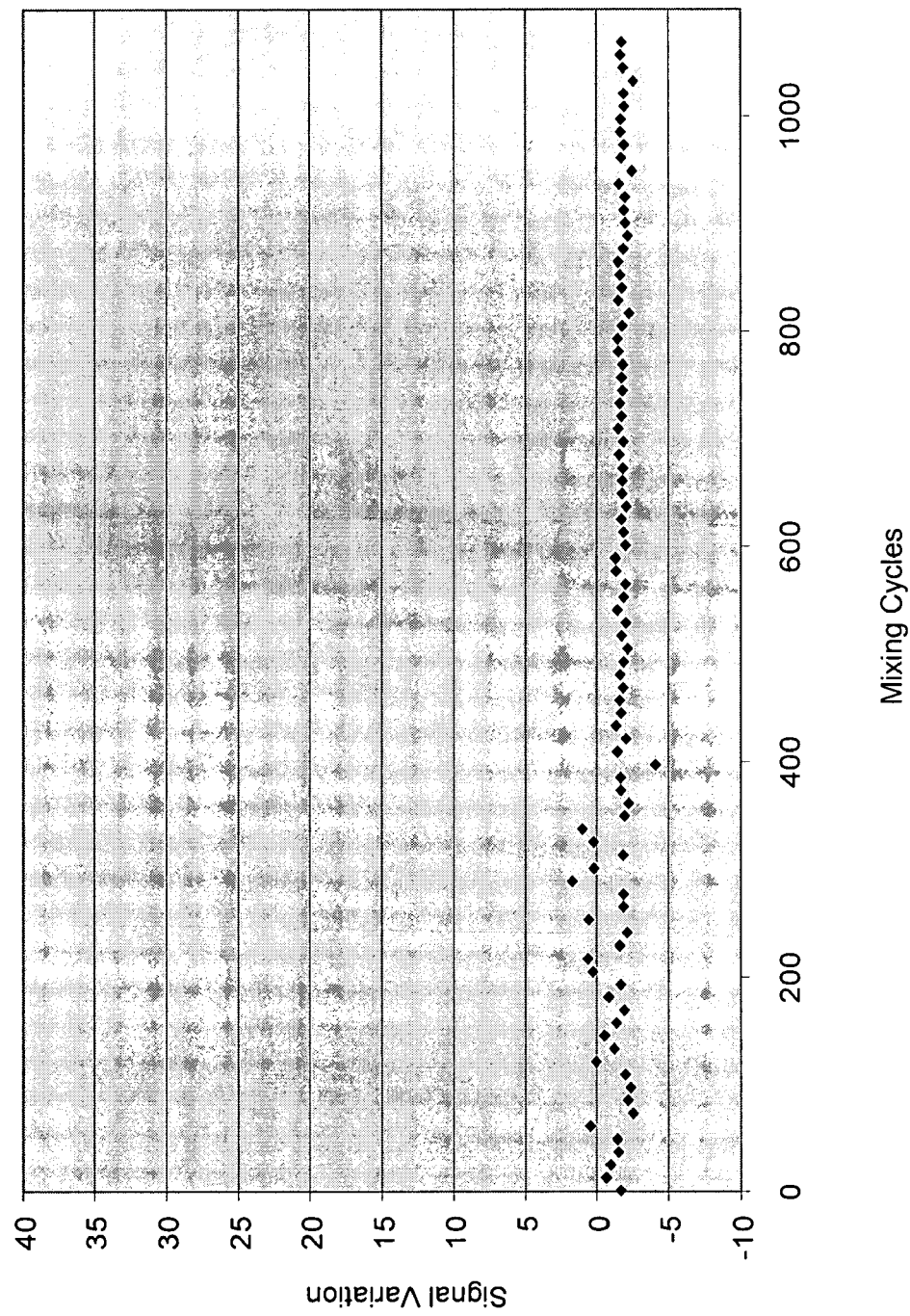

The significant increase in mixing efficiency that is achieved may be seen by measuring the variation in optical absorption of a dye mixture in water before and at the end of a given time interval, say 2-3 seconds, for different mixing methods. If the mixing method is highly effective, the variation or difference in absorption will be close to zero in less than 1 second because the water-dye solution will have essentially the same uniformity and the optical absorption will be unchanged. The amount of time required to reduce the variation in absorption to zero is thus an indication of the efficiency of the mixing method. FIG. 15 shows the difference in absorption of a water-dye solution for a prior art mixing technique in which a mixing probe is vibrated back-and-forth in a single linear direction. The difference is absorption does not begin to be close to zero until after one second of mixing, or approximately 150 "back-and-forth" mixing cycles where the probe sweeps through the entire length of the vessel. A roller mixing assembly 55 like seen in FIG. 14 and constructed with the electromagnet air gap 14G adjusted to achieve approximately ½ the stroke of the prior art mixing technique, in combination with adjusting the diameters of roller pin 86 and roller bearing 88 to achieve a generally parabolic or "boomerang-shaped" pattern, FIGS. 11 and 11A, has a significantly increased mixing efficiency as illustrated in FIG. 16. In contrast to the prior art, the roller mixing assembly 55 exemplary of the present invention is significantly more efficient, achieving close to zero difference in absorption in approximately 0.3 second, or 75 "boomerang-shaped" mixing cycles. The shorter required stroke of the roller mixing assembly provides the advantage of a reduced chance of the probe tip from striking the vessel wall, which has been shown to be a leading cause of the creation of bubbles and foaming while mixing.

Figure 17:
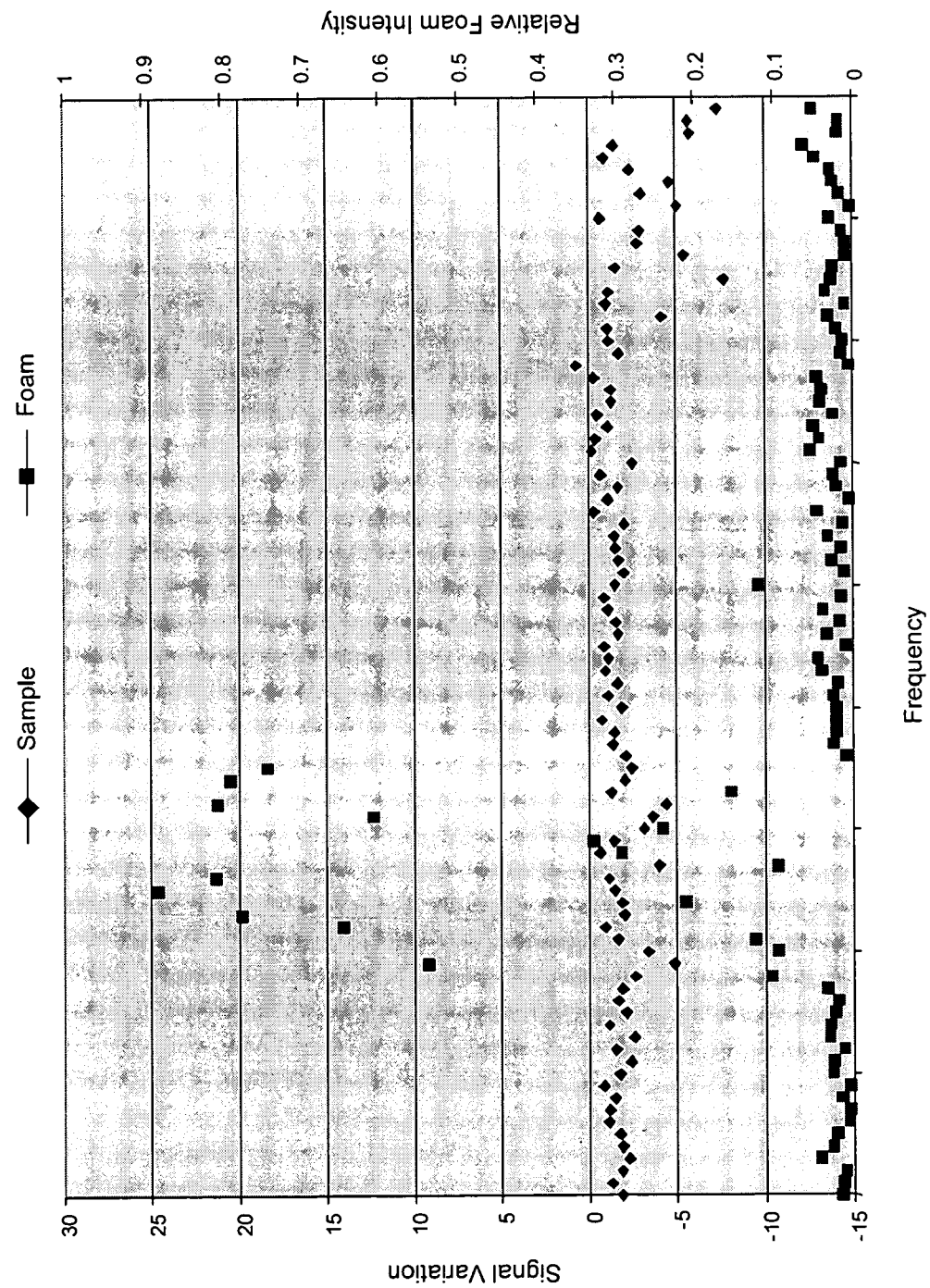
FIG. 17 is a second chart illustrating the mixing effectiveness of the roller mixing assembly exemplary of the present invention.

FIG. 17 illustrates another mixing parameter that affects the efficiency of roller mixing assembly 55. Depending upon a number of system parameters including the viscosity of liquid being mixed and the frequency at which roller mixing assembly 55 is operated which affects the displacement of the tip of needle probe 60N, foam may be generated within reaction cuvette 24. The frequency at which the tip of needle probes 54N, 60N and 62N is vibrated within this range is determined by the rate at which electromagnet 92 is "turned on and off". The presence of foam may be determined by measuring the variation in intensity of a 700 nanometer wavelength interrogating signal passing through reaction cuvette 24, the greater the variation being indicative of foam generated by the mixing action of roller mixing assembly 55. In FIG. 17, the adverse presence of foam is seen appearing as a large increase in signal at an operating frequency near the left one-third side of the chart.

Optimally, the design parameters of roller mixing assembly 55 are selected so that a "good" mix is achieved in 0.5 seconds or less and foam is not generated, a "good" mix defined as having signal variation less than 2% deviation from a zero baseline as seen in FIG. 16. What has been discovered is that, depending upon the stiffness of the probe to be used, the air gap 14G distance between electromagnet 92 and plate 91 must be adjusted to fall within a range that produces a displacement of the tip of needle probes 54N, 60N and 62N in a range from about 0.6 to about 1.2 mm. It has also been discovered that, depending upon the viscosity of the liquid to be mixed, the electromagnet 92 may be operated at different "on-off" frequencies in order to vary the mixing pattern and maximize the mixing efficiency of roller mixing assembly 55.

Figure 18:
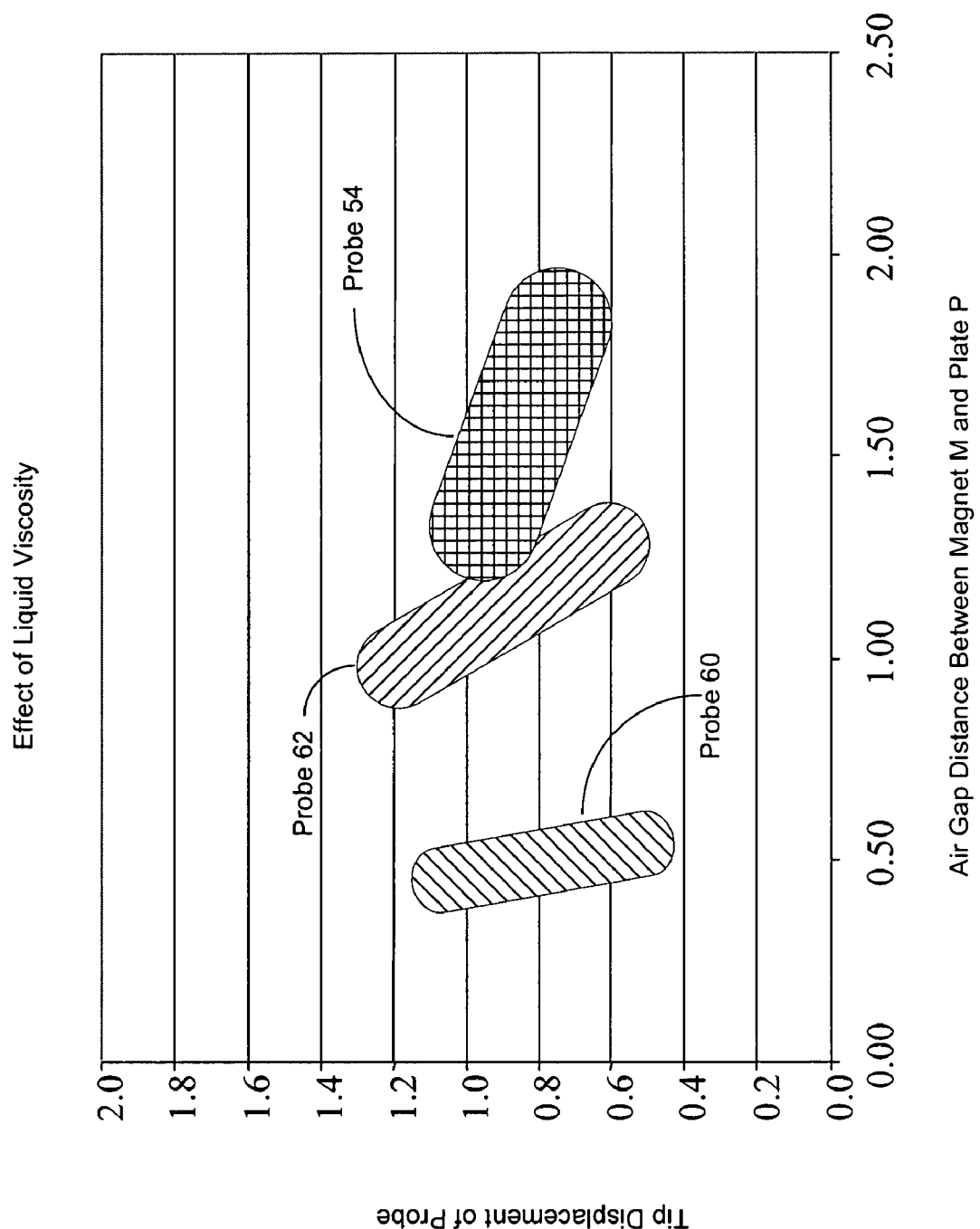
FIG. 18 is a chart illustrating a characteristic of the roller mixing assembly exemplary of the present invention.

In a typical embodiment, before sample is delivered to a reaction cuvette 24, a first reagent with a first viscosity is delivered to an empty reaction cuvette 24 and may be mixed before and/or after delivery, sample is then delivered to the reaction cuvette 24 containing first reagent and may be mixed before and/or after delivery, finally a second reagent may be delivered to reaction cuvette 24 already containing mixed sample and reagent and may be mixed before and/or after delivery. All of these liquids and mixtures generally will all have different viscosities and different volumes. Thus, the optimum design parameters and/or operating conditions will be different for the roller mixing assembly 55 associated with needle 54N to mix sample that has been retained in vessel 52V prior to delivery to a reaction cuvette and the roller mixing assembly 55 associated with needle 60N to delivery first reagent to an empty reaction cuvette and the roller mixing assembly 55 associated with needle 62N to add a second reagent and mix with an existing sample-first reagent mixture. This relationship may be seen in FIG. 18 illustrating three different air gap 14G distance ranges between electromagnet 92 and plate 91 required to maintain the displacement of the tip of probe needles 54N, 60N and 62N within about 0.6 to about 1.2 mm. Due to the inverse square nature of magnetic forces involved, if less force is required to achieve the 0.6-1.2 mm stroke, then a larger gap can be used, with an accompanying larger permissible variation in that gap, so that increased robustness and manufacturing tolerances are obtained. An artesian will appreciate that these values will change depending upon other design parameters, including the material of construction of, the length of, the diameter of, and the flexibility of probe needles 54N, 60N and 62. Irrespective of these variations, however, the use of a mixing assembly like roller mixing assembly 55 having a moveable arm 85 vibrated in a first direction so that roller pin 86 rolls along the circumference of roller bearing 88 and causes arm 86 to move side-to-side in a in a second direction, perpendicular to the first direction produces a "boomerang-shaped" mixing pattern of needle probe 60N that has been found to be surprisingly efficient in time and effective in mixing uniformity.

Table 1 below summarizes an exemplary set of operating conditions for an instance in which the sample probe 54 generally delivers body fluids like serum, first reagent probe 60 delivers reagents to a reaction cuvette 24 before sample is added thereto, and reagent probe 62 delivers reagents to a reaction cuvette 24 already having sample and reagent added and mixed therein.

TABLE 1

| PROBE | ELECTROMAGNET ON-OFF CYCLE | FREQUENCY | DUTY CYCLE | TIME |
|---|---|---|---|---|
| Probe 54 | 2 ms on, 2 ms off | 250 Hz | 50% | 0.5 sec |
| Probe 60 | 6 ms on, 3 ms off | 111 Hz | 67% | 0.5 sec |
| Probe 62 | 3 ms on, 1 ms off | 250 Hz | 75% | 0.5 sec |

It should be readily appreciated by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A mixing assembly for mixing solutions within a biochemical analyzer, the assembly comprising:
    a sampling probe needle depending from a moveable arm;
    an electromagnet proximate a ferromagnetic plate attached to the moveable arm for reciprocating the moveable arm in a first direction;
    a foot protruding from the moveable arm, the foot having a pin extending vertically upwards; and,
    a curved surface mounted to a stationary block and positioned in contact with said pin, whereby reciprocating the moveable arm in the first direction causes the pin to roll along the curved surface, whereby the moveable arm is reciprocated in a second direction perpendicular to said first direction.

2. The mixing assembly of claim 1 wherein the movement in the second direction is generally larger than movement in the first direction, thereby causing the probe needle to be moved in a generally ellipsoidal mixing pattern.

3. The mixing assembly of claim 1 wherein the movement in the second direction is generally twice as large as the dimension of movement in the first direction, thereby causing the probe needle to be moved in a generally "boomerang-shaped" mixing pattern.

4. The mixing assembly of claim 1 wherein the curved surface is a roller bearing or a stationary pin.

5. The mixing assembly of claim 1 wherein the distance between the electromagnet and the plate is adjusted to maintain the displacement of the probe needle to be within a range of about 0.6 to about 1.2 mm.

* * * * *

UNITED STATES PATENT AND TRADEMARK OFFICE
CERTIFICATE OF CORRECTION

PATENT NO. : 7,258,480 B2  Page 1 of 1
APPLICATION NO. : 11/032356
DATED : August 21, 2007
INVENTOR(S) : Dunfee et al.

It is certified that error appears in the above-identified patent and that said Letters Patent is hereby corrected as shown below:

1) On the title page in the left hand column, in the Inventors section (75); please delete "Hazlewood" and insert -- Hazelwood --.

Signed and Sealed this

Tenth Day of June, 2008

JON W. DUDAS
*Director of the United States Patent and Trademark Office*